United States Patent [19]

Sinaiko

[11] Patent Number: 5,643,229
[45] Date of Patent: Jul. 1, 1997

[54] SUCTION TUBE APPARATUS

[76] Inventor: Edwin S. Sinaiko, 180 E. Pearson, Chicago, Ill. 60611

[21] Appl. No.: 603,505

[22] Filed: Feb. 20, 1996

Related U.S. Application Data

[63] Continuation of Ser. No. 279,331, Jul. 22, 1994, abandoned.
[51] Int. Cl.⁶ .................................................. A61M 25/00
[52] U.S. Cl. ........................ 604/267; 604/174; 604/264
[58] Field of Search .............................. 604/35, 73, 128, 604/129, 174, 264, 267, 280, 284, 902; 433/91

[56] References Cited

U.S. PATENT DOCUMENTS

| | | | |
|---|---|---|---|
| 878,199 | 2/1908 | Freeman . | |
| 918,437 | 4/1909 | Genung . | |
| 954,494 | 4/1910 | Andrews . | |
| 958,854 | 5/1910 | Bunn . | |
| 1,485,298 | 2/1924 | Shroyer . | |
| 2,073,069 | 3/1937 | Lee .................................. | 27/24 |
| 2,137,635 | 11/1938 | Tyler ............................... | 27/24 |
| 2,492,384 | 12/1949 | Kaslow ..................... | 604/280 X |
| 3,958,573 | 5/1976 | Wiley ............................. | 128/276 |
| 4,699,138 | 10/1987 | Behrstock ................... | 128/207.16 |
| 5,084,012 | 1/1992 | Kelman ......................... | 604/35 |
| 5,154,696 | 10/1992 | Shearing ....................... | 604/22 |
| 5,197,949 | 3/1993 | Angsupanich ................ | 604/35 |
| 5,201,310 | 4/1993 | Turnbull .................... | 128/207.15 |
| 5,205,816 | 4/1993 | Dodson et al. ................. | 604/1 |
| 5,226,885 | 7/1993 | Takahashi .................... | 604/118 |
| 5,236,414 | 8/1993 | Takasu .......................... | 604/22 |
| 5,236,455 | 8/1993 | Wilk et al. .................... | 623/10 |
| 5,242,386 | 9/1993 | Holzer .......................... | 604/22 |
| 5,248,297 | 9/1993 | Takase .......................... | 604/22 |
| 5,254,117 | 10/1993 | Rigby et al. ................... | 606/46 |
| 5,257,620 | 11/1993 | Schermerhorn ............. | 128/200.26 |
| 5,261,893 | 11/1993 | Zamierowski ................ | 604/180 |
| 5,263,950 | 11/1993 | L'Esperance, Jr. ........... | 606/6 |
| 5,267,586 | 12/1993 | Jänkävaara ................... | 137/565 |
| 5,269,756 | 12/1993 | Dryden ......................... | 604/54 |
| 5,269,797 | 12/1993 | Bonati et al. ................. | 606/170 |
| 5,303,703 | 4/1994 | Monti-Bloch ................. | 128/642 |

*Primary Examiner*—Corrine M. McDermott
*Attorney, Agent, or Firm*—Dick and Harris

[57] ABSTRACT

An improved suction tube apparatus of the type which may be connected to a hose having a suction source attached thereto, for use, for example, during surgical procedures for the removal of blood and/or tissue from a surgical site, having an improved suction hose connection for facilitating prevention of inadvertent contact between the suction hose and any non-sterile areas in the operating room, for prevention of contamination of the suction hose, and thus of the suction tube apparatus, and/or sterile field.

7 Claims, 1 Drawing Sheet

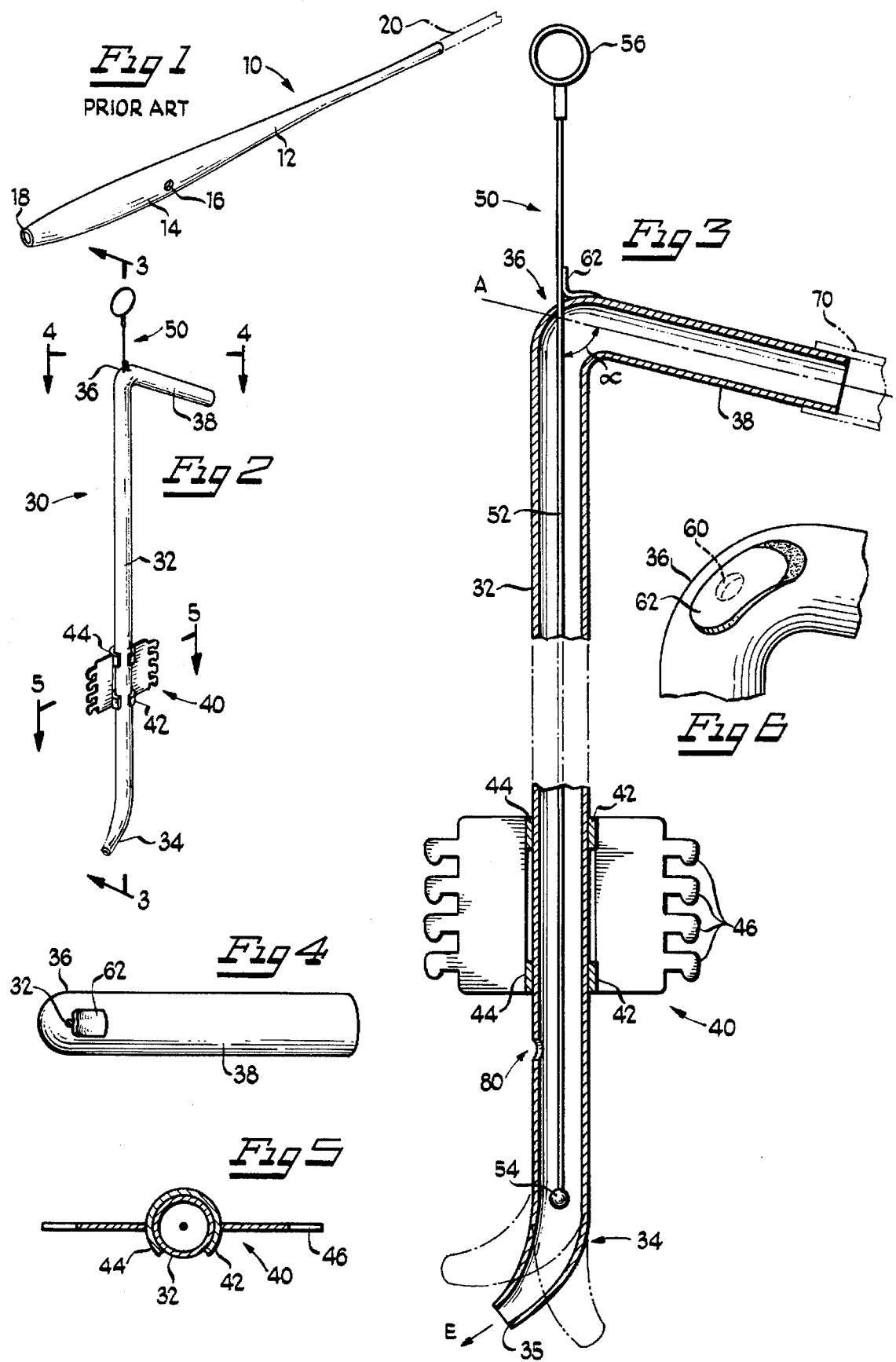

SUCTION TUBE APPARATUS

This is a file wrapper continuing application of application Ser. No. 08/279,331 filed Jul. 22, 1994, now hereby abandoned.

BACKGROUND OF THE INVENTION

The present invention is directed to suction tube apparatus, of the type which may be connected to a hose having a suction source attached thereto, for use, for example, during surgical procedures for the removal of blood and tissue from an operation site. Some prior art suction tube apparatus of this type are commonly known as Yankauer suction tubes.

A typical configuration of such a suction tube comprises a generally elongated tubular member, which may have central length of substantially constant inner and/or outer diameters. At one end of the tube is a tip which may be positioned into the operation site for the suction pick-up of blood, tissue, and so forth. The suction tube may also include a flared or widened portion along its length, which may facilitate grasping of the tube.

The other end of the tube may have a specific fitting for attachment to a hose, which is, in turn, connected to a suction source. Such attachment to the hose should be secure so as to prevent the loss of suction.

Along the length of the tube may be provided an aperture, which permits the in-flow of a small amount of air, when open, such that during typical operation procedures, the amount of suction being delivered to the tip is less than the maximum available amount being provided by the attached suction hose. During the operation procedure, when the surgeon desires a greater amount of suction in a particular instance, the surgeon, or an assistant, will grasp the suction tube so as to place a thumb over, or otherwise cover the aperture, thereby preventing in-flow of air at that location, and thus raising the amount of suction delivered to the tip to the maximum amount of suction being delivered by the suction hose.

One potential drawback to the construction of typical prior art suction tube apparatus is that the connection between the tube and the suction hose is either a straight direct connection, or is at only a very slight angle to the tube. This can present difficulties in that the hose which connects the tube to the suction source often extends upwardly of the operating table. As the surgeon or assistant moves the suction tube apparatus about in use, the suction hose may tend to swing about, with a substantial possibility of contact between the surgeon or assistant, and the hose, for example about the head and shoulders of the surgeon or assistant. If such contact occurs, according to standard operating room protocol, the hose, and suction tube contaminate the sterile field and should be replaced with one that is sterile, before the operation may continue.

Such a required replacement is troublesome in that the resultant lost time may be crucial with respect to the success of the operation, and/or the health of the patient. In addition, there is also the unnecessary cost involved in replacing the nonsterile parts.

It is desirable, therefore, to provide a suction tube apparatus which has an improved configuration which would reduce the likelihood of such inadvertent, nonsterile contact.

This and other objects of the invention will become apparent in light of the present specification, claims and drawings.

SUMMARY OF THE INVENTION

The present invention is an improved suction tube apparatus, of the type which may be connected to a hose having a suction source attached thereto, for use, for example, during surgical procedures for the removal of blood and tissue from an operation site.

The improved suction apparatus comprises a substantially elongated hollow tube having a first end, a second end, and a longitudinal axis; a suction tip operably connected to the first end of the hollow tube, in fluid communication therewith; a hose connection member operably connected to the second end of the hollow tube, in fluid communication therewith, and having a longitudinal axis, the hose connection member being operably arranged relative to the hollow tube such that the longitudinal axis of the hose connection member intersects the longitudinal axis of the hollow tube, with an included angle therebetween; and an elbow portion connecting the hollow tube to the hose connection member.

In a preferred embodiment of the invention, the included angle is in the range of 45° to 135°.

A preferred embodiment of the invention comprises an aperture operably disposed in said elbow portion, and substantially aligned with the longitudinal axis of the hollow tube; an obstruction clearing member, having an elongate configuration and a length exceeding a combined length of the hollow tube and the suction tip, the obstruction clearing member further having a first end and a second end, the obstruction clearing member further being insertingly receivable within the hollow tube, so as to extend along the combined length of the hollow tube and the suction tip, and have a portion extending through the aperture substantially beyond the intersection of the longitudinal axes of the hollow tube and the hose connection member, the first end of the obstruction clearing member being insertingly receivable in and through the suction tip, the second end of the obstruction clearing member being positioned in the portion extending through the aperture substantially beyond the intersection of the longitudinal axes of the hollow tube and the hose connection member.

The improved suction tube apparatus also comprises a push tip operably disposed at the first end of the obstruction clearing member, the push tip being operably configured so as to be able to pass through the aperture in the elbow portion; and a handle member operably disposed at the second end of the obstruction clearing member.

A cover member, may be operably disposed on the elbow portion of the apparatus, for covering and substantially closing the aperture in the elbow apparatus, when the obstruction clearing member is not insertingly received within the hollow tube.

Preferably, the suction tip is a normally curved, semiflexible member. The hollow tube, the hose connection member, and the suction tip are all formed as a contiguous tube member. The contiguous tube member is fabricated from a sterilizable plastics material. The contiguous tube member may be fabricated from a substantially transparent material. Alternatively, the contiguous tube member may be fabricated from a substantially translucent material.

The improved suction tube apparatus may also include a clamp member, removably and adjustably affixable to the hollow tube, and attachable to the body of a patient for stably and removably positioning the improved suction tube apparatus in position in an operation site.

BRIEF DESCRIPTION OF THE DRAWINGS

FIG. 1 is a perspective view of a prior art suction tube apparatus;

FIG. 2 is a perspective view of the improved suction tube apparatus according to the present invention;

FIG. 3 is a side elevation, partially in section, of the improved suction tube apparatus according to FIG. 2, taken generally along line 3—3;

FIG. 4 is a top plan view of the improved suction tube apparatus according to FIG. 2, with the clamp member omitted for clarity of illustration;

FIG. 5 is a top plan view, partially in section of the improved suction tube apparatus according to FIG. 2, taken generally along line 5—5; and FIG. 6 is a fragmentary perspective view of the elbow portion of the improved suction tube apparatus according to FIG. 2, showing the cover member in position to close the aperture in the elbow portion.

DETAILED DESCRIPTION OF THE INVENTION

While this invention is susceptible of embodiment in many different forms, there is shown in the drawings and will be described herein in detail, a single preferred embodiment, with the understanding that the present disclosure is to be considered as an exemplification of the principles of the invention and is not intended to limit the invention to the embodiment illustrated.

A prior art suction tube apparatus 10 is shown is FIG. 1. Suction tube apparatus 10 is a straight hollow tube 12 having a widened portion 14, which may be for grasping by the user. Aperture 16 is provided to act as a simple throttle, for controlling the amount of suction delivered to the tip 18. A suction hose, indicated by the broken lines at 20, is attached to end 22 of tube apparatus 10 by a simple friction fit, or by other known conventional means. Since hose 20 extends straight off of tube apparatus 10, there is increased potential for inadvertent contact between the hose and the user, during manipulation of tube apparatus 10.

Improved suction tube apparatus 30 is shown in FIGS. 2–6, and includes hollow tube 32, suction tip 34, elbow portion 36 and hose connector member 38. In a preferred embodiment of the invention, these components are all formed as a contiguous tube member, which may be of a plastic material, although other materials may be employed. In order for the functioning of the suction tube apparatus 30 to be monitored, the components are formed from translucent or transparent materials. Of course, these elements, as well as all other elements of suction tube apparatus 30 to be described hereinafter must be fabricated from materials which can be either manufactured in a sterile state, or later sterilized.

Clamp 40 is provided with gripping portions 42, 44, which permit clamp 40 to be "snapped" onto tube 32, at any appropriate desired location, such as by springing clamp 40, so as to cause gripping portions 42, 44 to "open". In this manner, the combination of clamp 40 with apparatus 30, can be used as a retractor, to hold back the tissues at variable distances to allow the surgeon access to the operative area. Other methods of attaching clamp 40 to tube 32 are also contemplated as being within the scope of this invention, so long as they allow clamp 40 to be positioned at varying positions along the length of tube 32, and can be removed entirely, for use when the area to be suctioned is a hole. It is additionally helpful to have the clamp 40 be adjustable so as to be able to accommodate variations in the thicknesses of the tissues being retracted. Such other methods may involve frictionally fitting rings, and the like. Clamp 40 is provided with hooks 46, for grasping the edges of the wound on the patient's person in the vicinity of the operation site, for positioning of the suction tube apparatus 30, when not being manipulated by the surgeon or an assistant. Clamp 40 is removable because at times it is necessary to insert tube 32 into some very tight areas.

During an operation procedure, suction apparatus 30 may become clogged with tissue or the like, and so such clogging material must be dislodged. Accordingly, obstruction clearing member 50 is provided. Obstruction clearing member 50 comprises an elongated rod 52 having a push member 54 at one end, and a handle 56 at the other end. The components of obstruction clearing member 50 may be fabricated from surgical stainless steel, or from surgical grade stiff plastic material, or other suitable material, so long as they are chemically nonreactive under operating conditions and may be made or rendered sterile.

In order to enable obstruction clearing member 50 to be inserted into hollow tube 32, aperture 60 is provided in elbow portion 36. Aperture 60 must have a sufficiently large diameter that push member 54 may be passed through without excessive difficulty. A flexible cover member 62 is attached to or formed as part of elbow portion 36, and biased so that it will tend to cover and close aperture 60, when obstruction clearing member 50 is not insertingly received within hollow tube 32. Alternatively, instead of flexible cover 62, which is attached or formed on elbow portion 36, aperture 60 may simply be covered by a sheet of material, such as a thin clear plastic sheet (not shown), which would be thin enough that it could be pierced by push member 54.

In order to enable the amount of suction delivered to suction opening 35 to be controlled, an aperture 80 is provided on 32, as indicated. Aperture 80 is sufficiently small that at least some suction is delivered to suction opening 35 at all times. However, when greater suction is desired, the surgeon or other operator will cover aperture 80, with a thumb, for example, and the suction will increase.

Suction tip 34 is tapered and may be fabricated to be normally curved in any of a number of possible desired positions, as indicated in FIG. 3. However, tip 34 is fabricated to be semi-flexible, both to facilitate its use in placement in various positions in the operation site to facilitate the pick up of fluids and debris, and to facilitate its cleaning and clearance from clogging material. In particular, in the event that suction tip 34 becomes clogged, obstruction clearing member 50 is inserted into and through aperture 60, until push member 54 comes into contact with the clogging material. Suction tip 34 will flex and bend back into a generally straight position (not shown) relative to hollow tube 34, to enable rod 52 and push member 54 to negotiate suction tip 34 and suction opening 35 to eject the clogging material outwardly, in the general direction of arrow E in FIG. 3. Push member 34 must therefore be sufficiently small in diameter relative to suction opening 35, that it can pass easily out of suction opening 35 during an unclogging procedure. Suction opening 35, in general, should be much larger than aperture 60, so that even when aperture 60 is open, and having rod 32 passing therethrough, the majority of the total amount of suction force delivered to suction tube apparatus 30 is directed to suction opening 35, and the amount of suction lost through aperture 60 is controlled. Of course, when obstruction clearing member 50 is not in place, and cover member 62 has returned to its usual biased position over aperture 60, the loss of suction through aperture 60 is substantially eliminated, since the suction in elbow portion 36 will then tend to keep cover member 62 in place closed over aperture 60.

In an alternative embodiment, as previously described, where cover member 62 is replaced with a simple, frangible plastic sheet, when obstruction clearing member 50 is in place, the sheet will tend to fit around clearing member 50, and tend to reduce the amount of lost suction through aperture 60. When clearing member 50 is not in place, the remnants of the sheet will tend to be drawn into aperture 60, and still tend to reduce the amount of lost suction.

Hose connection member 38 is provided on improved suction tube apparatus 30 for connection of a suction hose 70, shown in broken lines in FIG. 3. Typically, suction hose 70 would extend upwardly away from the suction tube apparatus to a connection to a suction source somewhere above the operating table. In order to help reduce the likelihood of inadvertent contact between the suction hose and the surgeon or assistant during manipulation of the suction tube apparatus 30, hose connection member 38 is configured such that the longitudinal axis A of hose connection member 38 intersects the longitudinal axis of hollow tube 32 (not shown, but which would extend parallel to rod 52 of obstruction clearing member 50, as illustrated in FIG. 3), with an included angle α therebetween the longitudinal axes in the range of 45° to 135°. By providing such a distinct downward turn to the connection, the suction hose will be forced to bow outwardly away from the surgeon or assistant manipulating the suction tube apparatus 30, and so the likelihood of inadvertent contact and contamination are reduced.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. An improved suction tube apparatus, of the type which may be connected to a hose having a suction source attached thereto, for use, for example, during surgical procedures for the removal of blood and tissue from an operation site containing both sterile and non-sterile objects, the improved suction tube apparatus comprising:

a substantially elongated hollow tube having a first end, a second end, and a longitudinal axis;

a substantially semi-flexible suction tip having an extreme end having a diameter which is less than the diameter of the hollow tube, and further being operably, substantially contiguously, formed to the first end of the hollow tube, in fluid communication therewith;

a hose connection member operably connected to the second end of the hollow tube, in fluid communication therewith, and having a longitudinal axis;

means for reducing inadvertent non-sterile hose contact such that the hose connection member is operably arranged relative to the hollow tube such that the longitudinal axis of the hose connection member intersects the longitudinal axis of the hollow tube, with an included angle therebetween of 45° and 135° so as to help reduce the likelihood of inadvertent contact between said hose and said non-sterile objects and resulting contamination;

said means for reducing inadvertent non-sterile hose contact including an elbow portion connecting the hollow tube to the hose connection member; and obstruction clearing means operably associated with said hollow tube for dislodging any clogging material from the interior of said hollow tube;

an aperture operably disposed in said elbow portion, and substantially aligned with the longitudinal axis of the hollow tube;

the obstruction clearing means including an obstruction clearing member, having an elongate configuration and a length exceeding a combined length of the hollow tube and the suction tip, the obstruction clearing member further having a first end and a second end;

the obstruction clearing member further being insertingly receivable within the hollow tube, through the aperture, so as to extend along the combined length of the hollow tube and the suction tip, substantially parallel to the longitudinal axis of the hollow tube, and have a portion extending through the aperture substantially beyond the intersection of the longitudinal axes of the hollow tube and the hose connection member, the first end of the obstruction clearing member being insertingly receivable in and through the suction tip, the second end of the obstruction clearing member being positioned in the portion extending through the aperture substantially beyond the intersection of the longitudinal axes of the hollow tube and the hose connection member;

the obstruction clearing member further having a push tip operably disposed at the first end thereof, the push tip being operably configured so as to be able to pass through the aperture in the elbow portion;

the obstruction clearing member further having a handle member operably disposed as the second end thereof; and a cover member, operably disposed on the elbow portion of the apparatus, for covering and substantially closing the aperture in the elbow portion when the obstruction clearing member is not insertingly received within the hollow tube.

2. The improved suction tube apparatus according to claim 1 wherein the suction tip is a normally curved, semi-flexible member.

3. The improved suction tube apparatus according to claim 1 wherein the hollow tube, the hose connection member and the suction tip are all formed as a contiguous tube member.

4. The improved suction tube apparatus according to claim 3 wherein the contiguous tube member is fabricated from a sterilizable plastics material.

5. The improved suction tube apparatus according to claim 4 wherein the plastics material is a substantially transparent material.

6. The improved suction tube apparatus according to claim 5 wherein the plastics material is a substantially translucent material.

7. The improved suction tube apparatus according to claim 1 and further comprising:

a clamp member, removably and adjustably affixable to the hollow tube, and attachable to the body of a patient for stably and removably positioning the improved suction tube apparatus in position in an operation site.

* * * * *